United States Patent [19]

Wieboldt et al.

[11] Patent Number: 5,045,703

[45] Date of Patent: Sep. 3, 1991

[54] COLD TRAPPING APPARATUS FOR INFRARED TRANSMISSION ANALYSIS INCLUDING A METHOD AND SUBSTRATE THEREFOR

[75] Inventors: Richard C. Wieboldt, Verona; Gregory E. Adams, Madison, both of Wis.

[73] Assignee: Nicolet Instrument Corporation, Madison, Wis.

[21] Appl. No.: 175,204

[22] Filed: Mar. 30, 1988

[51] Int. Cl.⁵ ........................ G01N 21/01; G01N 1/22
[52] U.S. Cl. .................................. 250/352; 250/304; 250/341; 356/38
[58] Field of Search ...................... 250/304, 352, 341; 356/36, 38; 73/61.1 C, 23.1

[56] References Cited

U.S. PATENT DOCUMENTS

| | | | |
|---|---|---|---|
| 4,158,722 | 6/1986 | Reedy | 250/338.1 |
| 4,448,524 | 5/1984 | Brus et al. | 356/36 |
| 4,594,226 | 6/1986 | Reedy | 422/89 |
| 4,632,553 | 12/1986 | Vidrine et al. | 356/346 |
| 4,688,936 | 8/1987 | Reedy | 250/352 |
| 4,823,009 | 4/1989 | Biemann et al. | 356/38 |
| 4,827,134 | 5/1989 | Willner et al. | 250/352 |

FOREIGN PATENT DOCUMENTS 87829   4/1987   Japan ..................................... 356/36

OTHER PUBLICATIONS

Hauge, R. H. et al., A Multisurface Matrix-Isolation Apparatus, *Applied Spectroscopy*, 40, No. 5, pp. 588-595, 1986.
Bourne, S. et al., Matrix Isolation GC/FTIR, *American Laboratory*, pp. 90-101, Jun. 1984.
Hembree, D. M. et al., Matrix Isolation Fourier Transform Infrared Spectrometric Detection in the Open Tubular Column Gas Chromatography of Polycyclic Aromatic Hydrocarbons, *Analytical Chemistry*, 53, No. 12, pp. 1783-1788, Oct. 1981.
Bourne, S. et al., Gas Chromatography/Matrix Isolation/Infrared Spectroscopy: An Evaluation of the Performance Potential, *Journal of Chromatographic Science*, 17, pp. 460-463, Aug. 1979.
Reedy, G. T. et al., Gas Chromatography/Infrared Matrix Isolation Spectroscopy, *Analytical Chemistry*, 51, No. 9, pp. 1535-1540, Aug. 1979.
Hastie, J. W. et al., Matrix Isolation Spectroscopy, in "Spectroscopy in Inorganic Chemistry," vol. 1, Edited by D. N. R. Rao and John R. Ferraro, *Academic Press*, New York, 1970, pp. 57-106.

*Primary Examiner*—Carolyn E. Fields
*Attorney, Agent, or Firm*—Foley & Lardner

[57] ABSTRACT

A gas sample collection device and method for cold trapping individual gas bands from a gas source that may include a chromatographic separation and for spectrographically analyzing the individual gas bands. The device includes a vacuum chamber containing a rotatably supported highly thermally conductive transmissive substrate having a highly thermally conductive support axle and at least one transmissive surface for holding a sample deposited thereon. A gas inlet is provided for depositing a mixture of sample and matrix material on the transmissive surface which is maintained at a sufficiently low temperature to cause solidification of the gas. A first set of optical elements directs an incident beam of electromagnetic analytical radiation from a source onto the solidified deposit, while a second set of optical elements directs the portion of incident beam transmitted through the deposit and substrate to a detector that is sensitive to the spectral wavelengths being investigated. A highly thermally conductive flexible strap is connected between the support axle and a cold head of a cryogenic refrigerator for transferring heat from the substrate. The strap is of sufficient length and flexibility to wrap around the axle as it is rotated through an angle of 360 degrees. A cold shield having closable apertures is provided for thermally insulating the substrate from warmer outside temperatures, the closable apertures being opened to allow access to the substrate for sample deposition and analysis. An insulated actuator is provided for imparting rotational movement to the axle and substrate assembly.

45 Claims, 3 Drawing Sheets

COLD TRAPPING APPARATUS FOR INFRARED TRANSMISSION ANALYSIS INCLUDING A METHOD AND SUBSTRATE THEREFOR

FIELD OF THE INVENTION

The invention relates to devices for studying chemical samples using the technique of cold trapping. In particular, the invention relates to devices which use cold trapping to connect a gas sample analyzer to a Fourier transform infrared spectrometer.

BACKGROUND OF THE INVENTION

Cold trapping of gaseous chemical samples is known to prior art. A chemical sample is heated to produce a vapor of gaseous sample molecules. The gaseous sample molecules are then combined with an excess of inert gas molecules, known as matrix molecules, and the gaseous mixture is directed onto the surface of a cold substrate. Upon contact with the substrate, the gaseous mixture condenses and freezes, forming a solid deposit on the substrate surface. The solid deposit, called a sample matrix, consists of a matrix formed by the inert molecules intermixed with a random scattering of sample molecules. The sample molecules in the matrix may then be studied using known chemical analysis techniques. In particular, if the substrate and the matrix are made of materials which are transparent to a particular range of electromagnetic radiation, for instance infrared, visible, or ultraviolet radiation, then a transmission absorption spectrum of the sample may be obtained with a suitable spectrometer. Because many important chemical transitions occur in the infrared spectral region, an infrared spectrometer, such as a Fourier transform infrared spectrometer, is usually preferred.

To prevent deleterious effects on the analysis, the sample molecules should be prevented from reacting with each other, or with residual molecules within the vacuum chamber enclosure, to form other compounds. To this end, the relative abundance of the sample molecules, compared to the number of inert matrix molecules, is kept rather low. Usually, the molecules of the sample make up less than one percent of the total molecules in the sample matrix. Because the percentage of sample molecules is so low, each sample molecule in the sample matrix is surrounded by a very large number of inert matrix molecules. The inert matrix molecules form a lattice within which the sample molecules are widely dispersed. This isolates the sample molecules from each other and also from other molecules which may be present in the vacuum chamber, and thereby inhibits the reactivity of the sample molecules. As a result, the technique is well suited to the spectral analysis of unstable or highly reactive molecules, such as free radicals and ionic metals.

To further reduce the reactivity of the sample molecules, the substrate on which they are deposited is cooled to cryogenic temperatures. Cryogenic temperatures, which are defined as being below zero degrees Celsius, reduce the thermal excitation level of the sample and thereby reduce the kinetic energy available for producing chemical reactions. Additional benefits of cryogenic cooling are an increased tendency for the sample matrix to solidify onto the substrate, rather than onto the inner walls of the vacuum chamber enclosure, and an improvement in the spectral quality of the absorption analysis due to a reduction in the peak broadening of the spectral lines.

Within the context of cold trapping, it has become desirable to combine this technique with other gas analysis techniques, particularly those which include gas chromatography, supercritical fluid chromatography or liquid chromatography. For instance, in gas chromatography the sample is passed through a gas chromatograph (GC) prior to being deposited onto the cold trap substrate. The function of the GC is to vaporize the sample and pass the gaseous sample molecules through a separating element. The separating element, usually a packed column or capillary tube, inhibits the flow rate of a molecule by a factor which depends upon the chemical composition of the molecule. As a result, when molecules of a multicomponent sample pass through the GC, they exit as a series of clusters, with each cluster consisting of molecules having essentially the same chemical composition. This concentrates the various components of the sample together and also separates them from each other in time as they leave the GC. A transfer tube, which terminates near the surface of the cold trap substrate, may then be used to carry the clusters of effluent from the GC to the substrate. The clusters of effluent may then be combined with matrix material and deposited in the usual way.

Since the effluent clusters exiting the GC are separated from each other in time and each cluster comprises a concentrated component of the original sample, it would be useful to be able to analyze the spectral profile of each cluster individually. Not only would the resulting spectral identification be simplified, because the sample has been broken down into its constituent components prior to spectral profiling, but the ease of identifying the sample components would be enhanced because the characteristic flow rate information from the GC could be used to augment the spectral information obtained for each cluster. Other devices, which may include the supercritical fluid chromatograph (SFC) or the liquid chromatograph (LC), would offer similar advantages when combined with cold trapping and infrared spectral analysis.

Unfortunately, while some have succeeded in doing this using a spectrometer which performs reflection measurements, no means has been devised to do this commercially using a substrate which is transmissive to infrared radiation. One reason that transmission measurements are preferred over reflection measurements is that the latter may be highly dependent on the morphology of the sample matrix deposit, while the former are not. Another reason is that reflection measurements involve two passes of the radiation through the sample, so sample thickness variations may cause considerable variation in the throughput of the instrument.

The reason that a transmission mode instrument has not been commercially successful is primarily because of a lack of a suitable substrate material. This largely results from the fact that the materials which are transparent to infrared radiation, materials which have traditionally consisted essentially of certain salts such as sodium chloride (NaCl), potassium bromide (KBr), and cesium iodide (CsI), have characteristics which make them extremely poor substrates for cold trapping.

First, these salts have poor mechanical characteristics. They are fragile, and thus easily broken; some are hygroscopic, and thus prone to permanent damage by fingerprints or prolonged exposure to moisture; and some are soft, and thus easily scratched. Optical grade elements are difficult and expensive to produce and may deteriorate very rapidly even after being installed in an artificial environment. Because the salts are soluble in many substances, including water, they can be difficult to work with and may be damaged merely by breathing on them. They may also be damaged if a corrosive effluent sample is deposited onto them. They may also tend to warp out of shape unless they are always kept in a vertical position, because when they are held horizontally they tend to sag in the center. They also tend to sag even if kept in a vertical position because they have a viscosity which allows them to flow very slowly. This physical property also limits the maximum size of the optical grade elements which can be produced. Furthermore, even small optical grade elements are very expensive, both in terms of the initial cost and in terms of the replacement cost which may be required.

Second, in addition to having poor mechanical characteristics, these materials are also extremely poor thermal conductors, which makes them ill suited for use as cold trap substrates. If the substrate is larger than a few square centimeters, the cryogenic cooling apparatus, which is usually a cryogenic refrigerator, may be unable to remove the heat produced by the condensation and solidification of the sample matrix. As a result, the transmissive substrates in current use are usually kept very small and they are mounted directly to the cold tip of the cryogenic refrigerator. A rigid copper frame is often used, together with gaskets made of indium, to increase heat flow from the substrate to the cold tip. Indium gaskets are used because the salt substrates are soluble in many of the thermally conductive pastes ordinarily used to increase heat transfer between connected elements. The copper frame and indium gasket increases the ability of the refrigerator to maintain the substrate at cryogenic temperatures, but causes difficulty if the substrate must be moved to enable cold trapping of more than one sample matrix. Moving the substrate may be important for other reasons. Often, the substrate position must alternate between a deposition position, where the sample matrix is deposited onto the substrate, and an analysis position, where the sample matrix is analyzed with the spectrometer. In addition, if an instrument such as a GC is used to separate the components of the sample prior to deposition, it is desirable to deposit the different effluent clusters on different regions of the substrate surface, and this requires that the substrate be moved relative to the terminal end of the transfer tube. However, if the substrate is rigidly fixed to the cold tip of the cryogenic refrigerator, as is the case with prior art designs, then the entire refrigerator must be moved in order to move the substrate and this requires elaborate and expensive cryogenic bearings which add further cost and complexity to the resulting instrument.

As a result of all of these difficulties, it is currently impractical to produce a general purpose cold trapping instrument which permits transmission absorption spectra to be obtained.

SUMMARY OF THE INVENTION

In accordance with the present invention, a semiconductor wafer is employed as a substrate for cold trapping. The semiconductor wafer is mounted within a vacuum chamber enclosure and is disposed to receive a vaporized sample. The wafer is supported for movement independent of a cryogenic refrigerator, yet possesses a thermally conductive rotatable support system which maintains good thermal conductivity with the cold tip of the refrigerator during movement of the wafer. The wafer may also be moved relative to the sample source, e.g. the terminal end of the transfer tube, in order to deposit sample material onto more than one location, and may be moved relative to the radiation beam of a spectrometer so that the locations where clusters are deposited may be individually positioned within the optical path of the spectrometer.

Additional objects, features, and advantages of the invention will be apparent from the following detailed description when taken in conjunction with the accompanying drawings.

DETAILED DESCRIPTION OF THE PREFERRED EMBODIMENT

Figure 1:
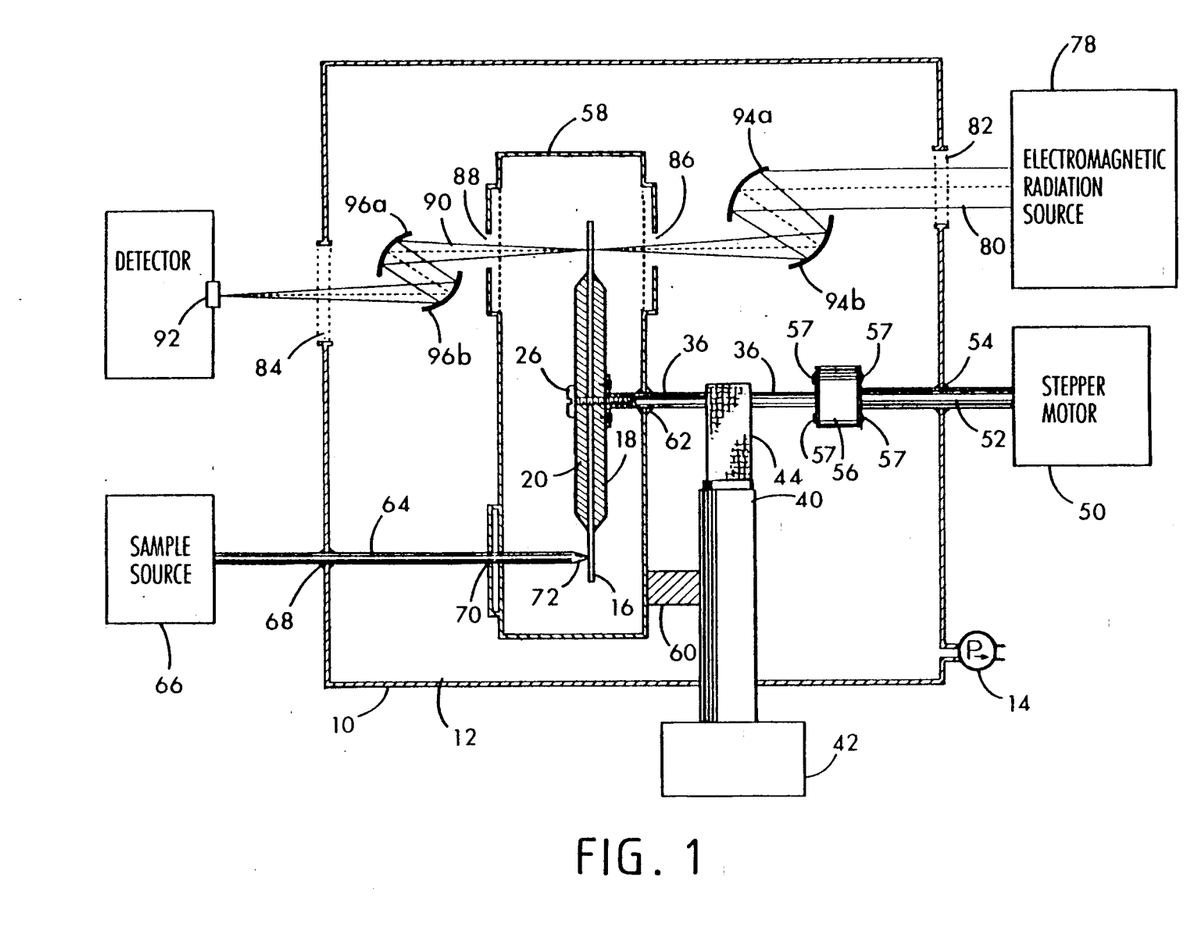
FIG. 1 is a side view of the preferred embodiment, with certain parts thereof shown in cross-section for purposes of illustration.

An enclosure 10 defines a vacuum chamber 12 which houses the elements that are cooled to cryogenic temperatures. The enclosure 10 is constructed to withstand internal pressures to below about $1 \times 10^{-9}$ Torr and is preferably made of stainless steel to minimize outgassing of molecules within the chamber when the chamber is evacuated. A vacuum pump 14 which communicates with the vacuum chamber 12 is used to evacuate the chamber to an internal pressure below about $1 \times 10^{-9}$ Torr. Vacuum pumps capable of evacuating the vacuum chamber 12 to such pressures are known to prior art and may include a mechanical vacuum pump which cooperates with a turbomolecular pump, a cryopump or a diffusion pump.

A substrate 16 is mounted within the vacuum chamber 12. The substrate 16 is made of a material which is rigid and which is transparent to the spectral region of interest. For infrared measurements, the substrate 16 preferably comprises a wafer made from a semiconductor material. Such wafers are commonly encountered in the semiconductor chip industry and are readily available at a reasonable cost. In the preferred embodiment, the substrate 16 is made of pure silicon, though other materials, including other semiconductors such as germanium and gallium arsenide, could also be used. Standard sizes usually range from about 4 to 8 inches in diameter and come in a variety of thicknesses.

If the substrate 16 is made of pure silicon, then substrate 16 preferably comprises a wafer having a substantially uniform thickness between about 0.5 mm and about 2.0 mm and a diameter of about 6 inches, and which is polished on both sides. In general, the diameter of the wafer is not critical to the operation of the invention and may accordingly be selected to suit availability or individual preferences. Factors that may also influence the chosen diameter may include, though not be exclusively limited to, the available cooling capacity provided to the substrate or the amount of sample that is sought to be deposited. Additionally, in connection with Fourier transform infrared spectroscopy, the thickness may need to be selected rather carefully because multiple reflections between the substantially parallel faces of the wafer may produce spurious signals which limit resolution. It is known to those in the art how to determine a thickness that will give a desired resolution; in the preferred embodiment the substrate thickness is about 1.0 mm. The availability of commercially produced semiconductor wafers for the electronics industry may provide a further influence on the dimensions of the wafer, low cost wafers being typically available in standard sizes of about 4 to 8 inch diameters and various thicknesses. It should be emphasized that other materials including, but not exclusively limited to, other semiconductors such as germanium and gallium arsenide, may be used instead of silicon.

Figure 2:
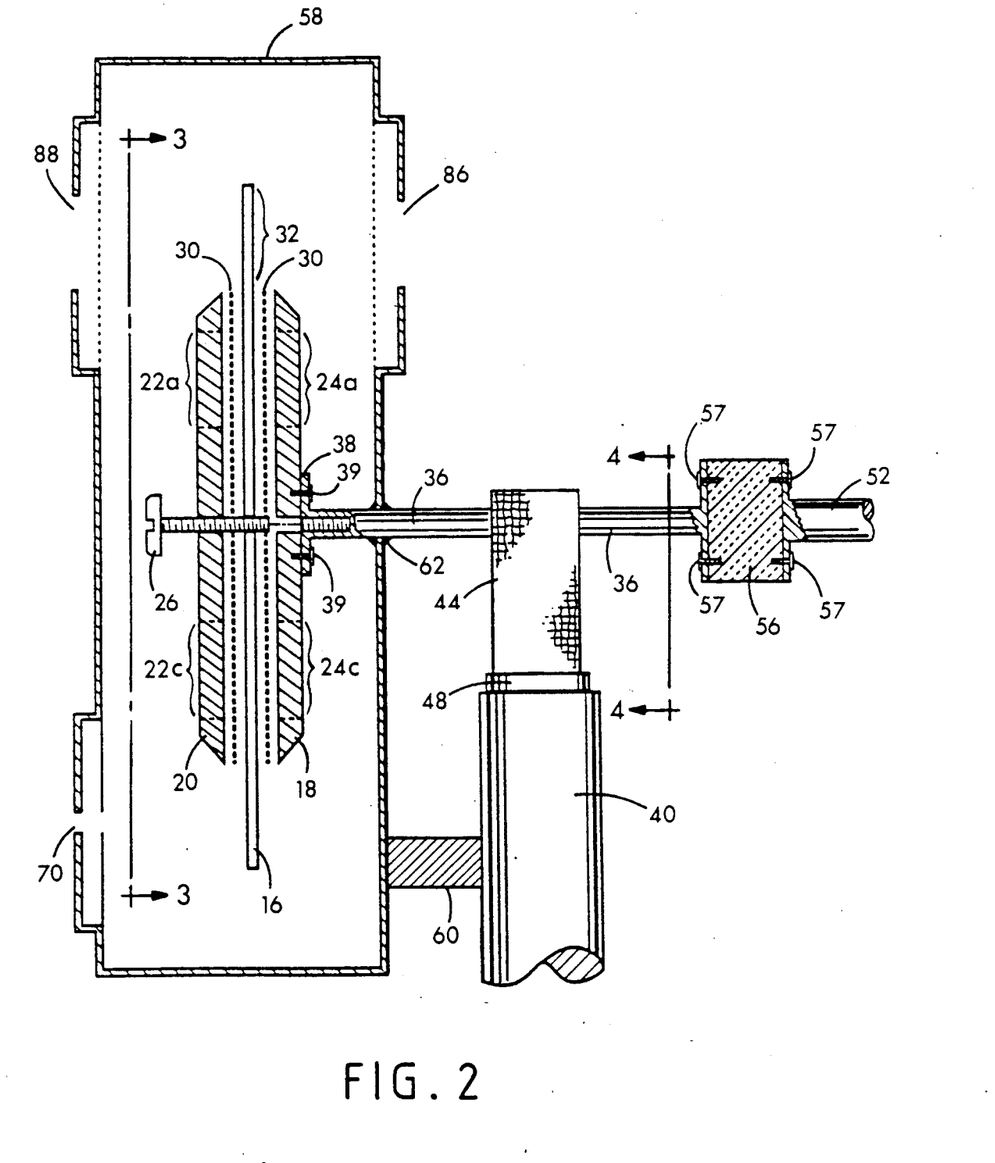
FIG. 2 is a side view of the substrate holder, with certain parts thereof shown in exploded relation and/or in cross-section for purposes of illustration, showing cryogenic and mechanical attachments.
Figure 3:
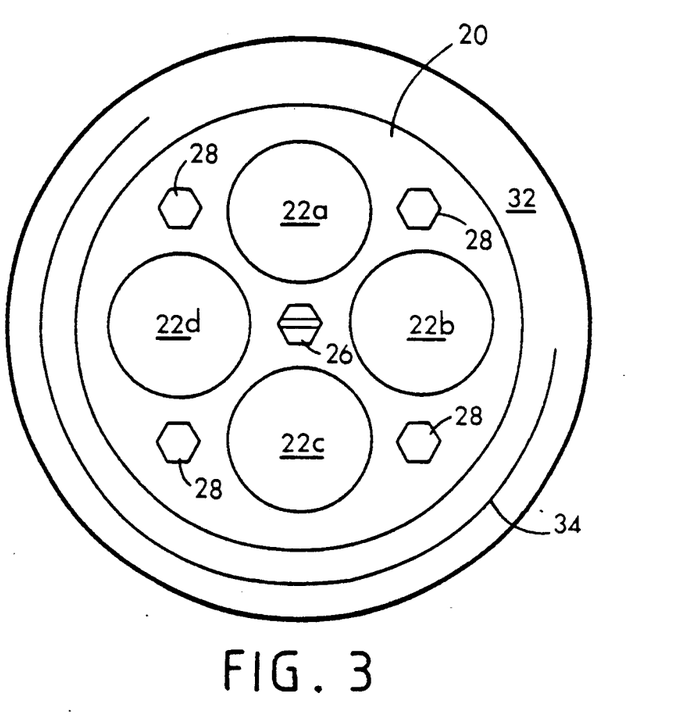
FIG. 3 is an end view of the substrate holder and cold trapped sample tracks taken generally along the line 3—3 of FIG. 2.
Figure 4:
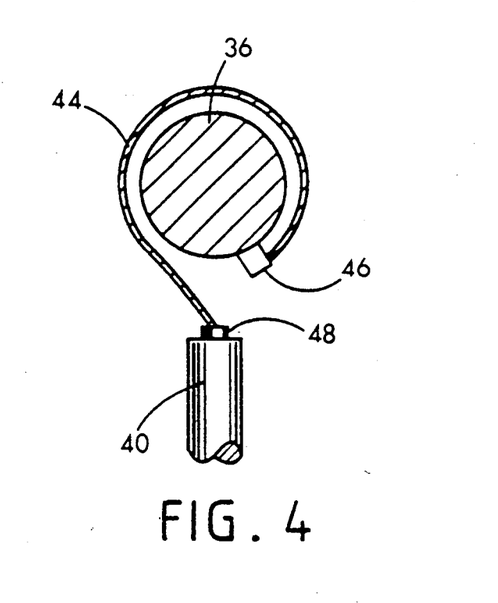
FIG. 4 is a cross-sectional view through the drive shaft and thermal conducting strap taken generally along the line 4—4 of FIG. 2.

The substrate 16 is rigidly mounted in a thermally conductive frame. In the preferred embodiment of the frame, the substrate is rigidly sandwiched between a first support plate 18 and a second support plate 20. Plates 18 and 20 are made of a highly thermally conductive material and are preferably made of a thermally conductive metal such as copper or brass. Holes 22a-22d, as shown in FIG. 3 and as indicated at 22a and 22c by dotted lines in FIG. 2, are cut in plate 18 to reduce its thermal mass. Similar holes 24a-24d, as indicated at 24a and 24c by dotted lines in FIG. 2, are cut in plate 20. A bolt 26 attaches plates 20 and 18 together through a clearance hole (not shown) in the substrate 16. Additional bolts 28, shown for illustration in FIG. 3, may be used to supplement or replace bolt 26. A thermally conductive paste 30, indicated by heavy dashed lines in FIG. 2, may be applied between plates 18 and 20 and substrate 16 to increase thermal conductivity between the adjoined surfaces. Alternatively, the wafer may be plated with a thermally conductive ductile material such as copper or indium to prevent gaps from forming between the wafer and the plates, it having been found that even small gaps will, under vacuum conditions, significantly reduce thermal conductivity between the wafer 16 and the plates 18 and 20.

Plates 18 and 20 have a diameter which is less than that of the substrate 16 so that, when assembled, an annular region 32 of the substrate 16 is exposed. This annular region of the substrate provides a transmissive surface region for holding the sample matrix. It is to be understood that the particular shape of plates 18 and 20 is not critical to the design of the invention and that many other frame designs, for instance radial spokes, perimeter frames or even spirals, may work equally well. However, in connection with matrix isolation of the effluent from a GC, it is preferred that the transmissive surface region be uninterrupted in order that effluent may be deposited in unbroken lines, such as in a manner suggested by trace 34. Continuous deposition is desired because a priori knowledge of when clusters will exit the GC may not usually be available. Of course, if a sample source other than a GC is used, or if for any other reasons it is desired, discontinuous transmission surface regions may be used without departing from the scope of the present invention. It should also be appreciated that the instant frame design may be suitable for holding a wide variety of transmissive substrates, including substrates which are transparent to electromagnetic wavelengths other than infrared.

The frame is rotatably supported by an axle 36. In the preferred embodiment, plate 18 is rigidly attached in good thermal contact to axle 36. The axle 36 is preferably made from a highly thermally conductive material, such as that used for construction of plates 18 and 20. The axle 36 may be attached to the plate 18 by various methods. Illustrated in FIG. 2 is the use of a flange 38 with a plurality of threaded fasteners 39. Equivalently, axle 36 may be integrally formed with the plate 18 or fastened by other suitable means known to the art.

In addition to rotatably supporting the frame, the axle 36 aids in the transfer of heat from the substrate 16 to a cold head 40 of a cryogenic refrigerator 42. In the preferred embodiment, heat transfer between the axle 36 and the cold head 40 is accomplished through a thermally conductive flexible strap 44. For purposes of this application, the strap 44 shall include coils, webs, braids, belts, springs or any other thermally conductive flexible elements that are woven or nonwoven and that comprise single or multiple layers of thermally conductive material, including copper or brass. These straps are known in the art; an example can be found in Hauge, R. H., et. al, "A Multisurface Matrix-Isolation Apparatus", *Applied Spectroscopy*, 40, #5, 1986.

The strap 44 is in good thermal contact with the axle 36 and with the cold head 40 and is preferably connected thereto by solder joints 46 and 48. Alternatively, other means may be used to secure the strap, such means being known to the art. Additionally, the strap 44 is of sufficient length and flexibility to enable the axle 36 to rotate a full 360 degrees about a longitudinal axis without restriction. FIG. 3 shows a cross-section of the axle 36, strap 44 and cold head 40 to illustrate the manner in which the strap 44 wraps around the axle 36 during rotation. Of course, the strap could be attached directly to part of the frame, e.g. plate 18 or 20, rather than to the axle 36. It would also be possible to employ an insulating frame and attach the strap directly to the substrate. Other thermally conductive flexible heat transfer methods may also be used.

Means for rotating the axle 36 is preferably provided by a stepper motor 50 having a drive shaft 52. Drive shaft 52 passes into the chamber 12 via an aperture 54 in a wall of the enclosure 10. Means for permitting the shaft 52 to rotate while simultaneously minimizing the ingress of outside air into the vacuum chamber 12 is known to prior art. An insulating block 56 is connected between axle 36 and drive shaft 52 to reduce thermal conductivity therebetween. A plurality of screws 57 may be used to provide mechanical connection between the axle 36, the shaft 52 and block 56. Other means for rotating axle 36, including but not limited to placing stepper motor 50 within the vacuum chamber 12, may also be used.

The cryogenic refrigerator 42 having cold head 40 is known to prior art. It is preferably a two stage refrigerator which has a first stage that reaches a temperature of about 77 degrees Kelvin and which has a second stage that reaches a temperature below about 12 degrees Kelvin. The second stage of the refrigerator communicates with the cold head 40 and thereby maintains the cold head 40 at a cryogenic temperature, preferably below about 12 degrees. Of course, other means for providing cryogenic temperatures to the vacuum chamber 12 are known to prior art, the preferred embodiment using a cryogenic refrigerator 42 is merely illustrative.

Within the context of the present invention, it is also understood that "cryogenic" is a term which refers to any temperature below zero degrees Celsius. Since some samples may solidify above about 12 degrees Kelvin, the invention may be practiced in a manner wherein cryogenic temperatures above about 12 degrees Kelvin are used. Thus, for purposes of the present invention, cryogenic temperatures shall not be limited to embodiments wherein the substrate is cooled to a temperature below about 12 degrees Kelvin and, instead, shall include embodiments wherein the substrate is cooled to any temperature below about zero degrees Celsius.

In the preferred embodiment, a cold shield 58 surrounds the substrate 16 to reduce the heat load on the substrate. By maintaining the shield 58 at cryogenic temperatures, any residual radiation within the enclosure 10 will preferably be absorbed by the shield 58 rather than by the substrate 16. To maintain the shield 58 at a cryogenic temperature, preferably about 77 degrees Kelvin, the shield 58 is thermally connected to the first stage of the cryogenic refrigerator 42 by a highly thermally conductive connector 60, which may comprise another strap similar to strap 44. However, connector 60 is different from strap 44 in that it need not necessarily be flexible as strap 44 should be. A means for securing the cold shield 58 in place is known to those in the art.

The cold shield 58 is provided with an aperture having a bearing 62 for allowing the axle 36 to pass therethrough. The bearing 62, preferably a precision ball bearing known to the art, is used to rotatably support the axle 36 within the aperture to permit smooth rotation of the axle 36 at cryogenic temperatures.

A transfer tube 64 communicates with a sample source 66 for passing effluent (not shown) from the sample source 66 to the vicinity of the substrate. In the preferred embodiment, the sample source 66 comprises a gas chromatographic analyzer, it being understood that the invention may also be practiced with other sample sources which do not employ a gas chromatographic analyzer. The transfer tube 64 penetrates a wall of the enclosure 10 and is sealed thereto by a bellows-type seal 68 of known construction, to prevent a loss of internal vacuum. The transfer tube 64 then penetrates the cold shield 58 through an aperture 70 and terminates in a deposition tip 72 which is located proximate to the transmissive surface region of the substrate 16. The transfer tube 64 is preferably a heated capillary tube of the type commonly used in GC, and preferably includes a fused silica transfer tube known to the art. The deposition tip 72 is also preferably made of fused silica. The terminal end of the deposition tip 72 is preferably positioned very close to the surface of the substrate 16, directly adjacent to the transmissive surface region. The terminal end of deposition tip 72 is preferably separated from the substrate 16 by a distance approximately equivalent to the diameter of the deposition tip opening. The sizes of such components are known to the art.

A source of electromagnetic radiation 78, preferably including a Fourier transform infrared spectrometer, directs a beam of electromagnetic radiation 80 to enter and exit the enclosure 10 via inlet window 82 and outlet window 84, respectively. If infrared radiation is to be employed, the windows 82 and 84 are transparent thereto and preferably comprise potassium bromide (KBr), cesium iodide (CsI), zinc selenide (ZnSe), or other infrared transparent window material known to the art. A first closable aperture 86 is provided in the cold shield 58 for allowing the beam of analytical radiation 80 to impinge upon the substrate 16. A second closable aperture 88 is provided in the shield 58 for allowing the transmitted portion 90 of the beam 80 to impinge upon a suitable radiation detector 92. Closable apertures 86 and 88 are known to the art. They are of a type which are suitable for use at cryogenic temperatures and are arranged so that they may be closed when access to the substrate is not needed.

Although the detector 92 could be mounted within the enclosure 10, thus eliminating the need for the outlet window 84, in the preferred embodiment the detector 92 is mounted outside the enclosure 10. Electromagnetic radiation detectors are known to prior art and, for infrared wavelengths, include mercury cadmium telluride (MCT) detectors. Optical elements 94a and 94b for reducing the size of the beam 80 may be used to adjust the spot size of the beam which strikes the substrate 16, it having been found that better spectrographic results may be achieved when the sample and the beam are both concentrated into small regions. Optical elements 96a and 96b collect the transmitted radiation 90 and focus it to the detector 92. Optical elements suitable for these purposes are known to the art and preferably comprise reflective off-axis paraboloids, but may include other elements having paraboloidal, spherical, helical, conical, cassegrainian or other shapes.

For purposes of illustration, the invention will be described as having a sample source 66 which includes a gas chromatograph. It is to be understood, of course, that the invention may be practiced with a sample source other than a GC. In particular, it is specifically contemplated that the invention may be used in conjunction with other analyzers such as the SFC, the LC, or other chromatographic analyzers. It should also be appreciated that the use of a semiconductor as a substrate for cold trapping is not limited to situations where the substrate is rotatable, it being specifically contemplated that the invention may be practiced in situations wherein the substrate is not movable or is indexed in some other manner, e.g. linearly translatable. Thus, the invention contemplates all situations wherein a semiconductor is used as a substrate for cold trapping.

During operation of the invention with a GC, a carrier gas, such as helium, continuously flows through the GC, the transfer tube 64 and the deposition tip 72. The carrier gas is uncondensable on the substrate 16 and is pumped away by the vacuum pump 14. A sample is introduced into the GC, which then separates the various components of the sample by impeding the flow of different components by different amounts. This produces a temporal separation of the various components as they exit from the GC and flow through the transfer tube 64 and deposition tip 72. An inert matrix gas, such as argon, may be added to the sample gas at some point prior to deposition. Upon striking the cold trap substrate 16 the sample material, together with any inert matrix gas which may have been added to the sample, condenses and freezes onto the transmissive surface region of the substrate 16, forming a deposit thereon. Simultaneously, the stepper motor 50 may be used to rotate the substrate so that the deposited material forms a substantially continuous trace 34. As temporally separated clusters leave the GC, they become deposited at different locations on the substrate 16. It is noted that the rates of carrier gas flow and motor rotation may be adjusted to provide optimal isolation or concentration of the clusters within the sample matrix. Additional adjustments to flow and rotation rates should be made to avoid heavy deposits of condensed material, it being known in the art that deposits more than about 0.5 mm thick may be prone to cracking and falling off the substrate.

After deposition, the traces 34 are examined with infrared radiation, preferably using a Fourier transform infrared spectrometer as previously described, to arrive at a characteristic profile for the deposit. Examination of a sample using this device is known to prior art, so only an outline will be given. Radiation 80 enters the enclosure 10 through transparent inlet window 82 and is focused by optical elements 94a and 94b onto a small region of the condensed material in trace 34. Radiation 90 which passes through the trace 34 and substrate 16 is collected by optical elements 96a and 96b and directed to the detector 92. Modulation of the radiation by the Fourier transform spectrometer leads to a modulation in the detected radiation. Analysis of the detected radiation permits a spectral profile of the material in trace 34 to be determined. This profile may then be compared to profiles of known materials to identify or otherwise study the constituents of the trace 34. In addition, the spectral profile information may be combined with the flow rate information established by the GC.

It is understood that the invention is not confined to the particular embodiments described herein as illustrative, but embraces such forms thereof as come within the scope of the following claims.

What is claimed is:

1. A rotatable cold trap support for supporting a transmissive substrate in a vacuum chamber enclosure, comprising:
    a) a transmissive substrate that is transmissive to a desired region of the electromagnetic spectrum;
    b) a frame which holds the transmissive substrate and which defines a transmissive surface region thereon;
    c) inlet means for depositing and solidifying a sample onto said transmissive surface region;
    d) a heat transfer means, in conductive communication with the transmissive substrate, for maintaining said transmissive surface region at a sufficiently low temperature to solidify the sample thereon, wherein the heat transfer means includes a flexible strap connected in thermal communication with the transmissive substrate, wherein the strap is made of a thermally conductive material;
    e) a rotatable support means for rotatably supporting the frame on a longitudinal axis; and
    f) a drive means, cooperating with the rotatably supported frame, for rotating the frame about said longitudinal axis.

2. The rotatable support of claim 1 wherein the frame is made of a thermally conductive material.

3. The rotatable support of claim 2 wherein the rotatable support means includes an axle connected to the frame, the axle being made of a thermally conductive material whereby the axle cooperates with the frame and with the heat transfer means to enhance heat transfer therebetween.

4. The rotatable support of claim 3 wherein the strap is of a sufficient length to permit the transmissive substrate to rotate through an angle of about 360 degrees.

5. The rotatable support of claim 4 wherein the frame includes a first plate rigidly connected to the axle, the first plate having a contact face that adjoins a first contact face of the transmissive substrate, the area of the contact face of the first plate being smaller than the area of the first contact face of the transmissive substrate.

6. The rotatable support of claim 5 wherein the frame includes a second plate having a contact face that adjoins a second contact face of the transmissive substrate, the area of the contact face of the second plate being smaller than the area of the second contact face of the transmissive substrate, whereby the first plate and the second plate define a transmissive surface region on the transmissive substrate.

7. The rotatable support of claim 6 including means for joining the plates to the transmissive substrate so that the adjoined surfaces thereof are in heat conductive contact.

8. The rotatable support of claim 7 wherein the transmissive substrate, the first plate, and the second plate are substantially circular and are coaxial with said longitudinal axis, the plates defining an annular transmissive surface region on the transmissive substrate.

9. The rotatable support of claim 8 wherein the drive means includes a stepper motor.

10. The rotatable support of claim 9 wherein the stepper motor includes a drive shaft terminating in a thermal insulator, said thermal insulator being disposed to transfer rotational motion from the drive shaft to the axle while inhibiting heat transfer therebetween.

11. A holder for holding a sample in a sample matrix, which comprises:
    a) a substantially pure semiconductor wafer having a thickness between about 0.5 mm and 2.0 mm and having a surface area of sufficient dimension to permit the wafer to hold the sample in a sample matrix;
    b) an indexed support means for movably supporting the semiconductor wafer; and
    c) heat transfer means, in thermal communication with the semiconductor wafer, for cooling the wafer to a sufficiently low temperature to solidify the sample, wherein the heat transfer means includes a flexible strap connected in thermal communication with the wafer, wherein the strap is made of a thermally conductive material.

12. The holder of claim 11 wherein the semiconductor wafer is made from a material taken from the group consisting of silicon, germanium, and gallium arsenide.

13. The holder of claim 11 wherein the semiconductor wafer is made of silicon.

14. The holder of claim 11 wherein the indexed support means includes means for rotatably supporting the semiconductor wafer.

15. A process for analyzing a sample held in a sample matrix, comprising the steps of:
    a) cooling a semiconductor substrate via a flexible strap connected in thermal communication with the substrate;
    b) depositing the sample onto a surface of the substrate to form a sample matrix;
    c) transmitting a beam of electromagnetic radiation through the sample matrix and substrate;
    d) collecting the portion of electromagnetic radiation transmitted through the sample matrix and substrate; and
    analyzing the collected portion of electromagnetic radiation to determine spectral features of the sample.

16. The process of claim 15 wherein the semiconductor substrate is made from a material taken from the group consisting of silicon, germanium, and gallium arsenide.

17. The process of claim 15 or 16 comprising the additional step of rotating the substrate about a longitudinal axis during said depositing step.

18. The process of claim 17 wherein said depositing step includes depositing the sample matrix on a annular portion of the rotating substrate.

19. The process of claim 18 wherein said transmitting step includes transmitting a beam of infrared radiation through the sample matrix and substrate.

20. The process of claim 19 wherein said analyzing step includes analyzing the collected portion of electromagnetic radiation with a Fourier transform infrared spectrometer.

21. The process of claim 20 comprising the additional step of cooling the substrate with a cryogenic refrigerator to a temperature below about 30 degrees Kelvin.

22. The process of claim 21 comprising the additional step of shielding the substrate with a cold shield.

23. The process of claim 15 or 16 comprising the additional step of indexing the substrate so that the sample matrix may be deposited onto more than one location on the substrate.

24. The process of claim 23 wherein said transmitting step includes transmitting a beam of infrared radiation through the sample matrix and substrate.

25. A device for holding a sample matrix, which comprises:
a) an enclosure having walls which define a vacuum chamber, including a means for evacuating gas from the chamber;
b) a semiconductor substrate wafer disposed within said vacuum chamber, the substrate wafer having a longitudinal axis and having a transmissive surface region which transmits infrared and wherein the substrate wafer is rotatably supported about said longitudinal axis;
c) inlet means for depositing and solidifying a sample onto said transmissive surface region of the substrate wafer; and
d) heat transfer means, in conductive communication with the wafer, for maintaining said transmissive surface region at a sufficiently low temperature to solidify the sample thereon, wherein the heat transfer means includes a flexible strap connected in thermal communication with the transmissive substrate, wherein the strap is made of a thermally conductive material.

26. The device of claim 25 further comprising drive means cooperating with the rotatably supported substrate wafer for selectively rotating the substrate wafer about said longitudinal axis.

27. The device of claim 25, wherein the substrate wafer is made from substantially pure silicon.

28. A device for holding a sample matrix, which comprises:
a) an enclosure having walls which define a vacuum chamber, including a means for evacuating gas from the chamber;
b) a semiconductor substrate wafer disposed within said vacuum chamber, the substrate wafer having a longitudinal axis and having a transmissive surface region which transmits infrared, wherein the substrate wafer is rotatably supported about said longitudinal axis and wherein the substrate wafer is made of substantially pure germanium;
c) inlet means for depositing and solidifying a sample onto said transmissive surface region of the substrate wafer; and
d) heat transfer means, in conductive communication with the wafer, for maintaining said transmissive surface region at a sufficiently low temperature to solidify the sample thereon, wherein the heat transfer means includes a flexible strap connected in thermal communication with the transmissive substrate, wherein the strap is made of a thermally conductive material.

29. A device for holding a sample matrix, which comprises:
a) an enclosure having walls which define a vacuum chamber, including a means for evacuating gas from the chamber;
b) a semiconductor substrate wafer disposed within said vacuum chamber, the substrate wafer having a longitudinal axis and having a transmissive surface region which transmits infrared, wherein the substrate wafer is rotatably supported about said longitudinal axis and wherein the substrate wafer is made of substantially pure gallium arsenide;
c) inlet means for depositing and solidifying a sample onto said transmissive surface region of the substrate wafer; and
d) heat transfer means, in conductive communication with the wafer, for maintaining said transmissive surface region at a sufficiently low temperature to solidify the sample thereon, wherein the heat transfer means includes a flexible strap connected in thermal communication with the transmissive substrate, wherein the strap is made of a thermally conductive material.

30. A device for holding a sample matrix, which comprises:
a) an enclosure having walls which define a vacuum chamber, including a means for evacuating gas from the chamber;
b) a semiconductor substrate wafer disposed within said vacuum chamber, the substrate wafer having a longitudinal axis and having a transmissive surface region which transmits infrared and wherein the substrate wafer is rotatably supported about said longitudinal axis, wherein heat transfer means are provided in conductive communication with the substrate wafer to maintain said transmissive surface region at a sufficiently low temperature to solidify the sample matrix onto said transmissive surface region and wherein:
a) the rotatably supported substrate wafer includes an axle made from a thermally conductive material;
b) the drive means includes means for thermally insulating the drive means from the axle; and
c) the heat transfer means includes a thermally conductive flexible strap connected at a first end to the axle and connected at a second end to a cryogenic cooling means, the strap having sufficient length and flexibility to allow the substrate wafer to rotate through an angle of about 360 degrees; and
c) inlet means for depositing and solidifying a sample onto said transmissive surface region of the substrate wafer.

31. The device of claim 30 further comprising shielding means for shielding the substrate wafer from contamination due to condensation of atmospheric impurities within the vacuum chamber.

32. The device of claim 31 wherein the shielding means comprises a cold shield that surrounds the substrate wafer and is thermally connected to the cryogenic cooling means, the cold shield having closable apertures for passing a beam of electromagnetic radiation to and from the sample.

33. The device of claim 31 wherein the shielding means comprises a cold shield, which surrounds the substrate wafer and which is in thermal contact with the cryogenic cooling means, having a first closable aperture for passing analytical radiation to the substrate, and having a second closable aperture for passing a transmitted portion of the radiation to a region outside the cold shield.

34. The device of claim 33 further comprising an optical window disposed within a wall of the enclosure for admitting the radiation into the vacuum chamber.

35. A system for cold trapping a sample for chromatographic analysis, which comprises:
  a) a device for holding the sample, which includes:
    i) an enclosure having walls which define a vacuum chamber, including a means for evacuating gas from the chamber;
    ii) a semiconductor substrate wafer disposed within said vacuum chamber, the substrate wafer having a longitudinal axis and having a transmissive surface region which transmits infrared radiation, wherein the substrate is rotatably supported about said longitudinal axis,
    iii) inlet means for depositing and solidifying the sample onto said transmissive surface region of the substrate, and
    iv) heat transfer means, in conductive communication with the substrate wafer, for maintaining said transmissive surface region at a sufficiently low temperature to solidify the sample onto said transmissive surface region, wherein the heat transfer means includes a flexible strap connected in thermal communication with the transmissive substrate, and wherein the strap is made of thermally conductive material; and
  b) a gas chromatograph, wherein the inlet means of the device for holding the sample is interconnected with the gas discharge of the chromatograph to provide clusters of gas samples for deposition onto respective areas of the transmissive surface region.

36. A system for cold trapping a sample for chromatographic analysis, which comprises:
  a) a device for holding the sample, which includes:
    i) an enclosure having walls which define a vacuum chamber, including a means for evacuating gas from the chamber;
    ii) a semiconductor substrate wafer disposed within said vacuum chamber, the substrate having a longitudinal axis and having a transmissive surface region which transmits infrared radiation, wherein the substrate is rotatably supported about said longitudinal axis,
    iii) inlet means for depositing and solidifying a sample onto said transmissive surface region of the substrate, and
    iv) heat transfer means, in conductive communication with the substrate wafer, for maintaining said transmissive surface region at a sufficiently low temperature to solidify the sample onto said transmissive surface region, wherein the heat transfer means includes a flexible strap connected in thermal communication with the transmissive substrate, and wherein the strap is made of thermally conductive material; and
  b) a supercritical fluid chromatograph, wherein the inlet means of the device for holding the sample is interconnected with the fluid discharge of the chromatograph to provide clusters of fluid samples for deposition onto respective areas of the transmissive surface region.

37. A system for cold trapping a sample for chromatographic analysis, which comprises:
  a) a device for holding the sample, which includes:
    i) an enclosure having walls which define a vacuum chamber, including a means for evacuating gas from the chamber,
    ii) a semiconductor substrate wafer disposed within said vacuum chamber, the substrate having a longitudinal axis and having a transmissive surface region which transmits infrared radiation, wherein the substrate is rotatably supported about said longitudinal axis,
    iii) inlet means for depositing and solidifying the sample onto said transmissive surface region of the substrate, and
    iv) heat transfer means, in conductive communication with the substrate wafer, for maintaining said transmissive surface region at a sufficiently low temperature to solidify the sample onto said transmissive surface region, wherein the heat transfer means includes a flexible strap connected in thermal communication with the transmissive substrate, and wherein the strap is made of thermally conductive material; and
  b) a liquid chromatograph, wherein the inlet means of the device for holding the sample is interconnected with the fluid discharge of the chromatograph to provide clusters of fluid samples for deposition onto respective areas of the transmissive surface region.

38. Apparatus for transmission analysis of a chemical sample comprising:
  a) an enclosure having walls which define a vacuum chamber, including means for evacuating gas from the chamber;
  b) a substrate that is disposed within the chamber and that is transmissive to a desired region of the electromagnetic spectrum;
  c) a frame which holds the substrate and which defines a transmissive surface region thereon;
  d) inlet means for depositing and solidifying a sample onto the transmissive surface region; and
  e) means for moving the frame to produce a trace of the solidified sample upon the transmissive surface region of the substrate;
  f) heat transfer means, in conductive communication with the substrate, for maintaining the transmissive surface region at a sufficiently low temperature to solidify the sample thereon, wherein the heat transfer means includes a flexible strap connected in thermal communication with the transmissive substrate, wherein the strap is made of thermally conductive material.

39. The apparatus of claim 38 wherein the frame is made of thermally conductive material.

40. The apparatus of claim 39 wherein the semiconductor wafer is a material taken from the group consisting of silicon, germanium and gallium arsenide.

41. The apparatus of claim 38 wherein the substrate is a semiconductor wafer.

42. The apparatus of claim 38 further including a electromagnetic radiation source that directs electromagnetic radiation through the trace of the sample and the transmissive surface region of the substrate.

43. The apparatus of claim 42 wherein the electromagnetic radiation source is an infrared radiation source.

44. The apparatus of claim 42 further including a detector that receives the radiation that has been directed through the trace of the sample and the transmissive surface region of the substrate for analysis.

45. A holder for holding a sample in a sample matrix, which comprises:
 a) a transmissive substrate that is transmissive to a desired region of the electromagnetic spectrum;
 b) an indexed support means for movably supporting the transmissive substrate; and
 c) heat transfer means, in thermal communication with the transmissive substrate, for cooling the substrate to a sufficiently low temperature to solidify the sample, wherein the heat transfer means includes a flexible strap connected in thermal communication with the substrate, wherein the strap is made of a thermally conductive material.

* * * * *